United States Patent [19]
Majors et al.

[11] Patent Number: 5,704,101
[45] Date of Patent: Jan. 6, 1998

[54] CREPED AND/OR APERTURED WEBS AND PROCESS FOR PRODUCING THE SAME

[75] Inventors: Mark Bruce Majors, Cumming; Benjamin John DeCorso, Woodstock; William Anthony Georger, Canton; Richard John Schmidt, Roswell; Howard Martin Welch; Gregory Alan Zelazoski, both of Woodstock, all of Ga.

[73] Assignee: Kimberly-Clark Worldwide, Inc., Neenah, Wis.

[21] Appl. No.: 463,592

[22] Filed: Jun. 5, 1995

[51] Int. Cl.$^6$ ................ B26F 1/24; B29C 59/04
[52] U.S. Cl. .............. 26/18.6; 26/18.5; 28/155; 28/163; 156/73.5; 156/515
[58] Field of Search .............. 26/18.6, 18.5; 28/155, 163; 156/73.5, 515

[56] References Cited

U.S. PATENT DOCUMENTS

| | | | |
|---|---|---|---|
| 1,494,262 | 5/1924 | Lorenz . | |
| 3,655,312 | 4/1972 | Erb et al. | 425/115 |
| 3,683,559 | 8/1972 | Kalwaites | 51/74 |
| 3,929,135 | 12/1975 | Thompson | 128/287 |
| 4,041,203 | 8/1977 | Brock et al. | 428/157 |
| 4,041,581 | 8/1977 | Diggle, Jr. | 26/18.6 |
| 4,469,734 | 9/1984 | Minto et al. | 428/134 |
| 4,487,796 | 12/1984 | Lloyd et al. | 428/154 |
| 4,689,862 | 9/1987 | Catallo | 26/18.6 |
| 4,710,186 | 12/1987 | DeRossett et al. | 604/383 |
| 4,758,297 | 7/1988 | Calligarich | 156/251 |
| 4,780,352 | 10/1988 | Palumbo | 428/138 |
| 4,781,962 | 11/1988 | Zamarripa et al. | 428/138 |
| 4,854,984 | 8/1989 | Ball et al. | 156/73.5 |
| 4,919,738 | 4/1990 | Ball et al. | 156/73.5 |
| 5,057,361 | 10/1991 | Sayovitz et al. | 428/290 |
| 5,336,552 | 8/1994 | Strack et al. | 428/224 |
| 5,366,782 | 11/1994 | Curro et al. | 428/137 |

FOREIGN PATENT DOCUMENTS

| | | |
|---|---|---|
| 0264676A1 | 4/1988 | European Pat. Off. . |
| 0409315A1 | 1/1991 | European Pat. Off. . |
| 0598970A1 | 6/1994 | European Pat. Off. .......... B26F 1/24 |
| 221777 | 5/1909 | Germany . |
| 2614160C3 | 4/1980 | Germany . |
| 94/08789 | 4/1994 | WIPO . |

*Primary Examiner*—John J. Calvert
*Attorney, Agent, or Firm*—Patrick C. Wilson; Nicholas N. Leach; James B. Robinson

[57] ABSTRACT

The present invention is directed to a process and apparatus for aperturing, creping and optionally laminating webs such as, for example, films and fibrous nonwovens. The present invention is also directed to the resultant materials. The process for aperturing and creping webs utilizes a pattern roll and an anvil roll with the anvil roll being rotated faster that the pattern roll. The resultant material is visually much different than conventional materials which are typically run through similar rolls wherein the pattern roll and anvil roll are run at the same speed or wherein the pattern roll is run faster than the anvil roll. The resultant materials have a wide variety of applications not the least of which includes a liner material for personal care absorbent articles such as diapers, training pants, feminine hygiene products, bandages and the like.

2 Claims, 6 Drawing Sheets

CREPED AND/OR APERTURED WEBS AND PROCESS FOR PRODUCING THE SAME

FIELD OF THE INVENTION

The present invention is directed to a process for creping and/or aperturing a web such as a film, a nonwoven web or a laminate as well as the materials produced by the process. More particularly, the present invention is directed to a process wherein the web is fed between a pair of counter-rotating pattern and anvil rolls wherein the smooth anvil roll is rotated faster than the pattern roll thereby yielding valuable properties in the resultant processed material.

BACKGROUND OF THE INVENTION

Almost all personal care absorbent articles include a liquid pervious body side liner material or top sheet, an absorbent core and some type of backing material or bottom sheet which is generally liquid impervious. In the area of feminine care products and in particular sanitary napkins, apertured films are frequently used as a top sheet due to the fact that they do not absorb fluids such as menses and therefore readily pass such liquids through to the absorbent core where they are absorbed and subsequently masked by the non-apertured areas in the film. This creates a relatively clean post-use appearance which is maintained provided there is little or no fluid flowback from the absorbent core to the surface of the liner.

One example of a product with a film cover used in such applications is a sanitary napkin manufactured by the Procter and Gamble Company of Cincinnati, Ohio. This product is marketed under the trademark Always® and is allegedly made in accordance with the teachings of U.S. Pat. No. 3,929,135 to Thompson which discloses vacuum aperturing of films which, according to the patent teachings, makes more of a three-dimensional material. Although the process produces a functional three-dimensional material, the types of substrates capable of being apertured and the line speeds possible are believed to be inherent limitations in vacuum aperturing processes of this type.

Another process for producing apertured films is taught in German Patent No. 26 14 160 to Endler and assigned to the Ramisch Company of Krefeld, West Germany. In this process a smooth backing roll and a patterned gravure roll are rotated at differential speeds with the pattern roll rotating at a faster rate than the smooth roll. A similar process is taught in European Patent Application No. 0 598 970 A1 to Giacometti and assigned to the Pantex Corporation of Pistoia, Italy. A wide range of substrates can be apertured using these types of processes at significant line speeds, however, the materials so apertured are relatively two-dimensional in nature and usually require an additional surge or transfer layer underneath to obtain acceptable fluid handling performance. In addition, because the pattern roll is moving faster, it tends to pull the material through the nip in between the two rolls and therefore stretches the material in the machine direction thereby exacerbating the two-dimensionality of the material.

Ball et al. U.S. Pat. Nos. 4,854,984 and 4,919,738 both disclose a dynamic mechanical bonding method and apparatus which bonds two or more materials together using a pattern roll and anvil roll either of which may be run faster than the other.

U.S. Pat. No. 4,469,734 to Minto and assigned to the Kimberly-Clark Corporation teaches the aperturing of meltblown nonwovens and U.S. Pat. No. 4,781,962 to Zamarripa et al. teaches a nonwoven and an apertured film bonded together using a pattern and anvil roll.

The foregoing processes can be used to aperture a variety of materials including films and fibrous nonwovens. Despite the foregoing teachings, there is still a need for additional materials which can be apertured and/or acted upon to increase their three-dimensional characteristics. Materials which are three-dimensional give the appearance of being more cloth-like and aesthetically pleasing. This has been a common shortcoming of many apertured films which are often characterized as having a "plastic feel" and look. As a result, there is a need for materials and processes for forming the same which can be fluid pervious and more cloth-like in appearance. These and other needs are satisfied by the materials and process of the present invention as will become more apparent from a further review of the following specification, drawings and claims.

SUMMARY OF THE INVENTION

Figure 1:
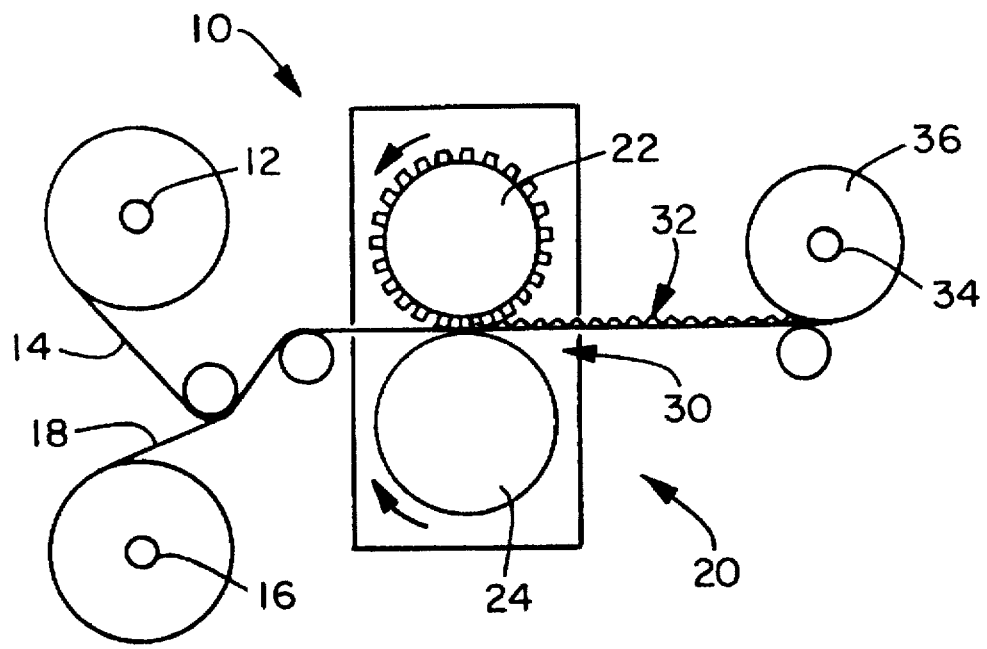
FIG. 1 is a schematic side view of a process and apparatus according to the present invention which can be used for aperturing, creping and/or laminating various materials.

The present invention is directed to a process and apparatus for aperturing and/or creping a web material such as a film, a fibrous nonwoven or a laminate of such materials or other materials. When running two or more materials through the process of the present invention at the same time, it is possible to laminate them too. The present invention also relates to the resultant materials which have been creped and/or apertured.

The apparatus includes a pattern roll and an anvil roll either or both of which may be heated and/or cooled to facilitate the processes of creping, aperturing and laminating. The surface of the pattern roll has a plurality of raised and/or depressed areas to create a three-dimensional surface wherein only select areas of the surface contact the web material passing through the nip area defined between the pattern roll and the anvil roll. The anvil roll has a flat surface when compared to the pattern roll.

The pattern roll and the anvil roll are rotated in opposite directions to one another so as to draw the web material through the nip area defined therebetween. The first or pattern roll will have a first rotational speed and the second or anvil roll will have a second rotational speed. The second rotational speed of the anvil roll will be greater than the first rotational speed of the pattern roll.

One or more webs of material are unwound and fed into the nip area between the counterrotating pattern and anvil rolls. The inlet speed of the web or webs may be adjusted to be less than, equal to or greater than the first rotational speed of the pattern roll. Once the web or webs exit the nip area they are wound up on a windup roll. The withdrawal speed of the web or webs from the nip area may be adjusted to be equal to or greater than the first rotational speed of the pattern roll and less than or equal to the second rotational speed of the anvil roll.

Depending upon the speed differential between the pattern roll and the anvil roll as well as the nip pressure between the two rolls, various attributes can be imparted to the web or webs being processed. Generally the rotational speed of the anvil roll will be at least about 1.8 times faster than the rotational speed of the pattern roll. In other situations the speed of the anvil roll may be as much as six or more times the speed of the pattern roll. Increasing the speed differential will increase the amount of crepe in the material being processed. As a result, the web entering the nip area, which may be single or multiple layers of material, will have a first basis weight and a second basis weight as it exits the nip which will be greater than the first basis weight. The speed differential coupled with the nip pressure will also increase the shear rate between the two rolls thereby increasing the aperturing capability of the process. Generally the nip pressure will range between about 2.0 and about 6.0 kilograms per lineal millimeter.

If desired, two or more web materials may be run through the nip at the same time. Depending upon the process conditions chosen, the materials may be laminated, creped, apertured or a combination of the foregoing. The resultant materials have a wide variety of applications not the least of which include a body side liner or backing material for personal care absorbent articles such as diapers, training pants, incontinence devices, wipes, bandages and feminine care products such as sanitary napkins, pantiliners and the like. These products will typically include a liquid pervious top sheet and a bottom sheet with an absorbent core disposed therebetween. The top sheet may comprise the material or materials of the present invention. The same is also true with respect to the bottom sheet and other components of the product.

DETAILED DESCRIPTION OF THE INVENTION

Referring to FIG. 1, the process of the present invention is shown in schematic form using a side-elevational view. The apparatus for the process is represented generally as element 10. The apparatus 10 includes a first web unwind 12 for a first web 14 and an optional second web unwind 16 for a second web 18. For purposes of illustration only, the first web unwind 12 shall be described as having a roll of plastic film and the second web unwind 16 shall be described as having a roll of fibrous nonwoven web material such as a spunbond, meltblown or bonded carded web as well as an air laid or wet laid web. It should be understood, however, the unwinds 12 and 16 may be used to feed any type of web material into the process which is compatible with the equipment and objects of the present invention. In order to further manipulate the properties of the materials formed by way of the present invention, it has been found advantageous to control the speed of the unwinds 12 and 16. As a result, it is desirable to provide each of the unwinds with driving and/or braking means (not shown) to control the speed of the unwinds as will be explained in further detail below. Such driving and/or braking means are widely known and commonly used in conjunction with such unwinds to control tension.

The first web 14 or simply "web" if only one unwind is being used is taken off the unwind 12 and is passed into a creping and aperturing assembly 20 which includes a first or patterned roll 22 and a second or an anvil roll 24 both of which are driven and/or braked with respect to one another so as to create a speed differential between the two rolls 22 and 24. Suitable means for driving the patterned roll 22 and the anvil roll 24 include, for example, electric motors (not shown).

Figure 2:
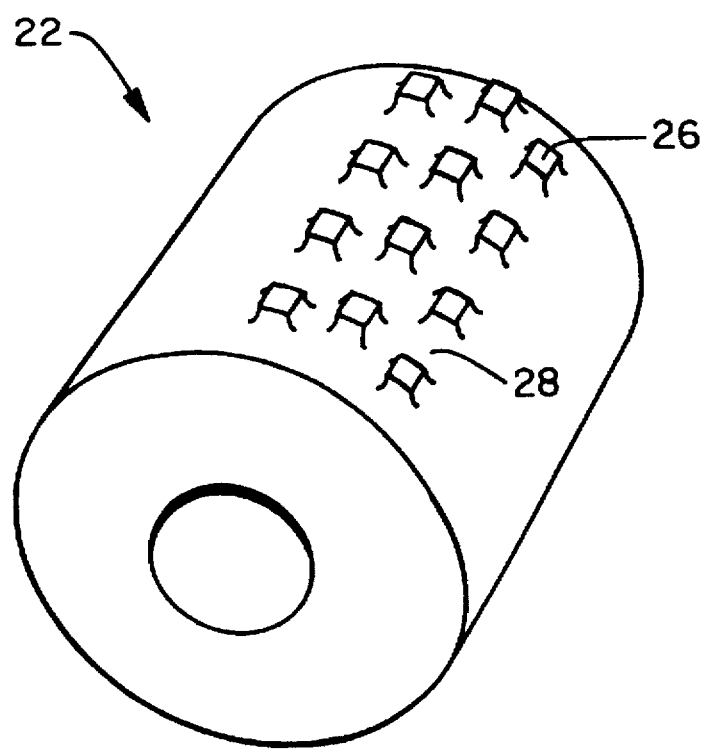
FIG. 2 is a partial perspective view of a pattern roll which can be used in accordance with the process and apparatus according to the present invention.

The patterned roll 22 is typically made from a durable material such as steel to reduce the wear on the roll as much as possible. The patterned roll 22 has a pattern of raised areas 26 separated by a pattern of depressed areas 28. See FIG. 2. The raised areas 26 are designed to contact the surface of the anvil roll 24. The size, shape, pattern and number of raised areas 26 on the pattern roll 22 can be varied to meet the particular end-use needs of the user. Typically the relative percentage of raised areas per unit area of the roll will range between about 5 and about 50 percent and the average contact area of each of the raised areas 26 will range between about 0.20 and about 1.6 square millimeters. Generally, the height of the raised areas 26 can range between about 0.25 and about 1.1 millimeters though heights outside this range can be used for specific applications if so desired. As a result, the number of contact areas per unit area of the pattern roll 22 will generally range between about 3 and about 100 raised areas per square centimeter of the roll. The footprint or shape of the raised areas 26 on the pattern roll 22 can also be varied. Ovals, squares, circles and diamonds are several examples of shapes that can be used.

Unlike the prior apparatus and processes which ran the pattern roll faster than the anvil roll, when the anvil roll is run faster than the pattern roll, a much different material is created. By running the anvil roll 24 faster, the material being sent through the process is compacted by the anvil roll 24 against and between the raised areas 26 on the pattern roll 22 thereby causing creping and increasing the basis weight of the material. The degree of creping will depend in part upon the speed differential of the two rolls, the wind up speed and the area (spacing and depth) between the raised areas 26. It has been found, for example, that a pattern roll 22 with large surface area pins and a high density will produce a more open and visually apparent apertured film than when using smaller raised areas 26 or pins and a lower density.

Another desired feature of the pattern roll 22 is that its temperature can be varied (heated or cooled) relative to the anvil roll 24. Heating and or cooling can affect the features of the web and/or the degree of bonding if multiple webs are being run through the process at the same time. Common heating techniques include hot oil and electrical resistance heating.

The anvil roll 24 is characterized in that its surface is much smoother than the pattern roll 22 and preferably is flat.

It is also possible, however, that the anvil or second roll 24 may have a slight pattern in it and still be considered flat for purposes of the present invention. For example, if the anvil roll is made from or has a softer surface such as resin impregnated cotton or rubber, it will develop surface irregularities yet will still be considered flat for purposes of the present invention. Such surfaces are collectively referred to as "flat." The anvil roll 24 provides the base for the pattern roll 22 and the web material to shear against. Typically the anvil roll 24 will be made from steel or materials such as hardened rubber, resin-treated cotton or polyurethane. The composition, degree of tack and hardness of the anvil roll 24 will impact the shape of the resulting apertures in the web 32.

The anvil roll 24 also may have flat areas separated by depressed areas (not shown) so that only select areas of the anvil roll 24 will contact the pattern roll 22. The same technique may be used on the pattern roll 22. As a result, aperturing and/or creping can be selectively imparted to specific regions of the web being processed. As with the pattern roll 22, the anvil roll 24 may be heated and/or cooled to further affect the properties of the web being processed.

The pattern roll 22 and the anvil roll 24 are counterrotated at differential speeds to create varying types of materials. The first or pattern roll 22 is rotated at a first rotational speed measured at its surface and the second or anvil roll 24 is rotated at a second rotational speed measured at its surface. In all cases, however, the anvil roll 24 is rotated at a faster speed than the pattern roll 22. The positioning of the two rolls with respect to one another may be varied to create a nip area 30 between the pattern roll 22 and the anvil roll 24. The nip pressure can be varied depending upon the properties of the web itself and the type of aperturing and creping desired. Other factors which will allow variances in the nip pressure will include the speed differential between the pattern roll 22 and the anvil roll 24, the temperature of the rolls and the size and spacing of the raised areas 26. For such materials as films and nonwovens, the nip pressure will range between about 2.0 and about 6.0 kilograms per lineal millimeter (kg/1 mm). Other pressures are also possible depending upon the particular end use.

The differential speed between the pattern roll 22 and the anvil roll 24 causes a shear between the raised areas 26 on the pattern roll 22 and the anvil surface on the anvil roll 24 which scores the web and creates apertures through the web 14. If the speed differential is increased further, the incoming web begins to bunch up in and around the raised areas 26 of the pattern roll 22 thereby creping the web as it passes through the nip area 30. Once the web 14 has gone through web creping and aperturing assembly 20 its features and contours are changed significantly as shown by the photomicrographs of the materials set forth in the examples below. As the web 14 leaves the creping and aperturing assembly 20, the apertured and/or creped web 32 is collected on the web winder 34. The web winder collects the creped and/or apertured web 32. As with the first unwind 12 and the second unwind 16, the winder 34 is driven by an electric motor or other drive source which can be varied so as to adjust the speed at which the finished web 32 is wound up into a roll 36. As will be explained in further detail below, the speed at which the web 32 is wound on the winder 34 will also affect the properties and appearance of the web 32. Alternatively, the web winder 34 may be eliminated and the web 32 may continue in line (not shown) for further processing as, for example, conversion into a liner material for a personal care absorbent article.

Both the inlet speed and the withdrawal speed of the web or webs 14 can be varied to change the conditions of the process. For example, the inlet speed of the web 14 can be equal to or faster than the first or pattern roll 22. Its speed also can be equal to or slower than the rotational speed of the second or anvil roll 24. Exiting the nip area 30 the web, webs or laminate can have a withdrawal speed which is equal to or faster than the first roll and slower or equal to the rotational speed of the second roll.

In addition to running just a single web 14 through the apparatus and process 10 shown in FIG. 1, it is also possible to run multiple webs through the same apparatus 10, provided one or more additional unwinds such as the second unwind 16 are added to the machinery. For example, the first unwind 12 may be fitted with a film and the second unwind 16 may be fitted with the same or a different material such as a fibrous nonwoven web 18. The two webs 14 and 18 are fed into the creping and aperturing assembly 20 in the same manner as before. Due to the increased thickness of material, the nip pressure and heating conditions may have to be varied to achieve the desired results and appearance in the laminate 32 formed by joining the two webs 14 and 18 together. If aperturing of the film in a film and nonwoven combination is desired, it is generally more advantageous to position the film layer 14 adjacent the pattern roll 22.

Having described the process, a series of sample single layer and multi-layer web laminates were formed to further illustrate the present invention. The samples and the test methods used to evaluate them are set forth below.

TEST METHODS

Several test methods were employed in determining the properties of the materials according to the present invention. The methods for determining these properties are set forth below.

BASIS WEIGHT

The basis weights of the various materials described herein were determined in accordance with Federal Test Method Number 191A/5041. Sample size for the specimens was 15.24×15.24 centimeters and three values were obtained for each material and then averaged. The values reported below are for the average.

THICKNESS

The thickness of the materials including laminates was measured using the Starrett Bulk test. Under this test a 12.7×12.7 centimeter sample of the material was compressed under a load of 0.05 pounds per square inch (3.5 grams per square centimeter) and the thickness was measured while under this load. Higher numbers indicate a thicker material. Five samples were measured for each material and then averaged. Values given are for the average.

POROSITY

The Frazier air permeability of the materials was determined in accordance with Federal Test Method Number 191A/5450. Five specimens of each material were tested and then averaged to obtain the reported values.

SURFACE TOPOGRAPHY (PROFILOMETER TEST)

The surface of many of the materials according to the present invention had enhanced topography due to the process of the present invention. By running the anvil roll faster than the pattern roll the web material being processed is compacted within the nip area. Due to mechanical pressure and optional heating, the web material can be both creped and apertured. This creped and apertured material was found to have enhanced aesthetic acceptance due to its ability to channel fluids from its top surface down through to its bottom surface. The surface of the materials according to the present invention exhibited a relatively high topography which was irregular in design. As shown by the profilometry data below, the standard deviation of the film cross-sections between apertures was quite irregular from aperture to aperture.

Stylus profilometry is a test method which allows measurements of the surface irregularity of a material using a stylus which is drawn across the surface of a material. As the stylus moves across the material, data is generated and is fed into a computer to track the surface profile sensed by the stylus. This information can in turn be plotted to show the degree of deviation from a standard reference line and thus demonstrate the degree of irregularity of a material. Surface profilometry data was generated for Examples 1 through 4 and is set forth below. This data was then plotted in FIG. 8.

The film surfaces of the materials in Examples 1 through 4 were scanned using a Rank Taylor Talysurf Laser Interferometric Stylus Profilometer model from Rank Taylor Hobson Ltd. of Leicester, England. The stylus used a diamond tip with a nominal 2 micron radius (Part #112/1836). Prior to data collection, the stylus was calibrated against a highly polished tungsten carbide steel ball standard of known radius (22.0008 millimeters) and finish (Part #112/1844). During testing, the vertical position of the stylus tip was detected by a helium/neon laser interferometer pick-up (Part #112/2033). The data were collected and processed using Form Talysurf Version 5.02 software running on an IBM PC compatible computer. The stylus tip was drawn across the sample surface at a speed of 0.5 millimeters per minute and over a distance of 1.25 millimeters. The test characterized the longer wavelength structure of the surface of the films between the apertures. The paths tracked by the stylus of the profilometer were across the top surface of the materials from aperture to aperture. The average profile waviness (Wa) was determined for each film from ten individual scans taken from aperture to aperture.

To perform the procedure, a 5 millimeter by 5 millimeter scan consisting of 256 datalogged profiles was taken from the top surface of each film using the diamond tip stylus. The surface data was filtered using a 0.25 millimeter wave filter which rejected the finest surface detail but retained the longer wavelength structure.

Figure 8:
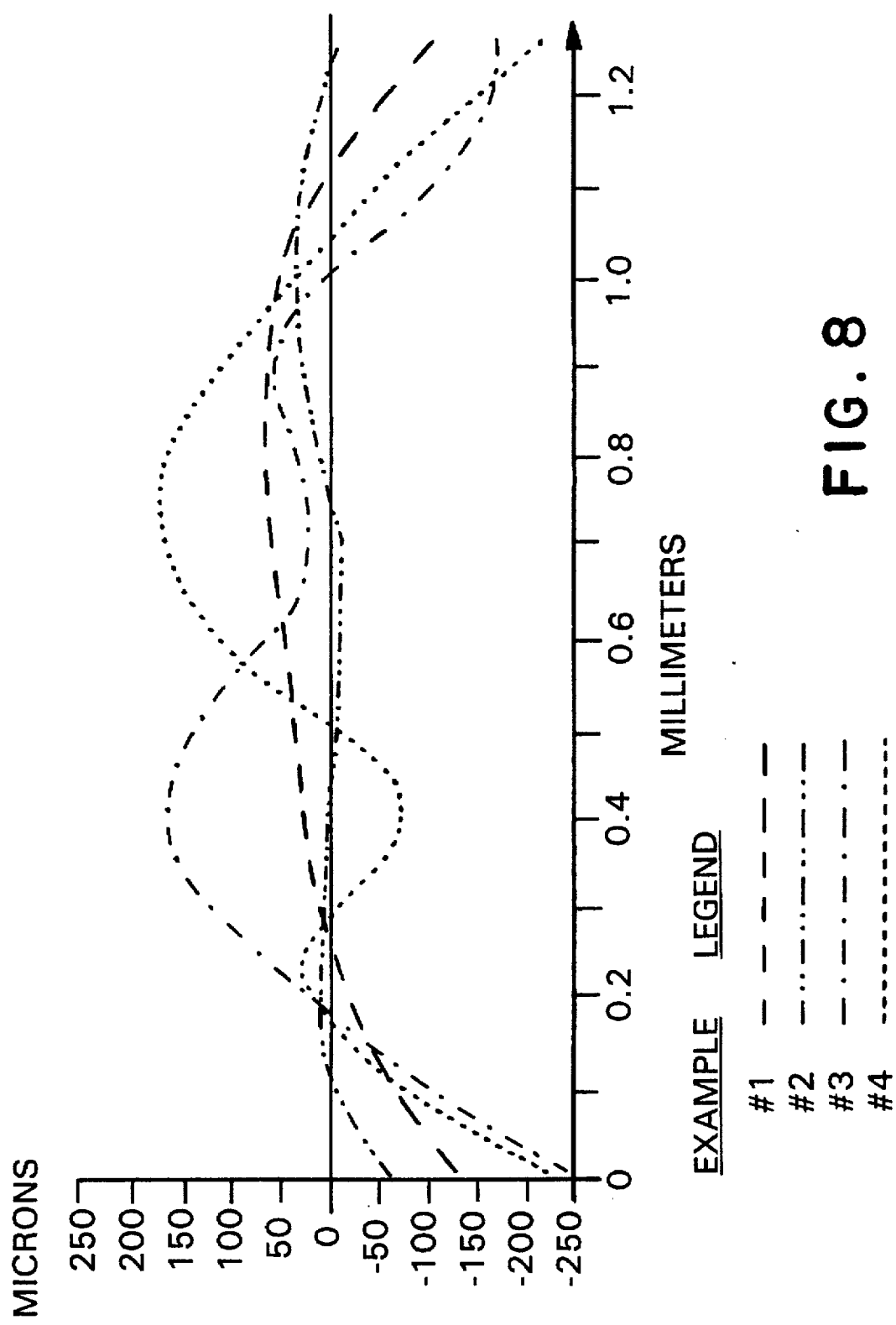
FIG. 8 is a graph of the profilometry data generated with respect to the materials in Examples 1 through 4.

Ten profiles were extracted from the wave-filtered surfaces. Average profiles for each set of ten profiles were plotted on the same 500 micron vertical scale for a measured distance of about 1.25 millimeters and are shown in FIG. 8 along with the mean Waviness (Wa) and standard deviation values which define the convoluted structure of the film between the apertures.

EXAMPLES

A total of five examples are set forth below. In Examples 1 through 3 the web 14 was a thermoplastic film. In Example 4 there were two webs used including a thermoplastic film and a fibrous nonwoven web. In Example 5 the web was a fibrous nonwoven web.

The film used in Examples 1 through 3 had a thickness or bulk of 0.025 millimeters. Its composition included, on a weight percent basis based upon the total weight of the web, 76 percent NA-206 low density polyethylene (LDPE) with a density of 0.918 grams per cubic centimeter ($g/cm^3$) and a melt index of 13.0 grams per 10 minutes at 190° C. under a load of 2160 grams. The polymer is available from Quantum Incorporated of Wallingford, Conn. The remaining portion of the composition was 24 weight percent titanium dioxide ($TiO_2$) concentrate which included 50 weight percent $TiO_2$ and 50 weight percent low density polyethylene carrier thus making the total weight percent of $TiO_2$ in the film 12 percent and the remaining 88 percent LDPE. The $TiO_2$ is available from the Ampacet Company of Mount Vernon, N.Y. under the grade designation 41171.

In Example 4 the film was a 0.019 millimeter thick cast film containing on a weight percent basis based upon the total weight of the film, 94 percent of the above-described NA-206 LLDPE and 6 percent of a titanium dioxide concentrate (grade designation 110313) from the Ampacet Company. This concentrate included 70 weight percent $TiO_2$ and 30 weight percent LDPE carrier resin. Thus the effective $TiO_2$ concentration in the film was 4 weight percent and the LDPE concentration was 96 percent.

The fibrous nonwoven web used in Example 4 was a spunbond web made from side-by-side bicomponent fibers. The fibers comprised approximately 50 weight percent Dow grade 6811A polyethylene from the Dow Chemical Company of Midland, Mich. and approximately 50 weight percent Exxon 3445 polypropylene from the Exxon Chemical Company of Darien, Conn. The fibers so produced were essentially continuous in nature and had an average fiber diameter of 22 microns. The nonwoven web had a basis weight of 16.6 grams per square meter (gsm) and the fibers of the nonwoven web were treated with Y12488 polyalkylene oxide-modified polydimethylsiloxane non-ionic surfactant wetting package from OSi Specialties, Inc. of Danbury, Conn. This package references U.S. Pat. No. 5,057,361. The surfactant addition to the nonwoven web was 0.4 percent based upon the total dry weight of the web. For more information on forming bicomponent spunbond webs see U.S. Pat. No. 5,336,552 to Strack et al. which is incorporated herein by reference in its entirety.

In Example 5 the fibrous nonwoven web used was a three layer prebonded composite of spunbond, meltblown and spunbond webs with the meltblown web in the middle. The laminate included a 7.0 gsm meltblown layer between two layers of approximately 10.5 gsm spunbond material for a total laminate weight of 28 gsm. The spunbond fibers were approximately 20 microns in diameter and the meltblown fibers were approximately 3 microns in diameter. The laminate was point bonded with a bond area of approximately 15 percent and approximately 48 bond points per square centimeter. The spunbond resin was grade PF-304 polypropylene from Himont U.S.A., Inc. and the meltblown resin was grade 3746G polypropylene from the Exxon Chemical Company. An example of how to form such a laminate can be found in Brock et al. U.S. Pat. No. 4,041,203 which is incorporated herein by reference in its entirety.

The equipment used to aperture the webs in the examples was similar to that described above. Three different bond pattern rolls were used. The pattern roll for Examples 1, 2 and 5 used diamond-shaped pins set in offset rows. The pin specifications included a pin height of 0.38 mm, equal axis lengths of 1.06 mm, total pin surface area of 1.12 $mm^2$, a pin density of 30.3 pins per square centimeter and a total bond or contact area of 35 percent. The patterned roll used in Example 3 was similar to the one just described in that the pins were also diamond-shaped in offset rows with the difference being the pin dimensions and density. The pins used on this roll had a pin height of 0.42 mm, equal axis lengths of 0.85 mm, total pin surface area of 0.72 $mm^2$, a pin density of 42.2 pins per $cm^2$ and a total bond or contact area of 31 percent. For Example 4 the patterned roll used round pins set in a random pattern not in uniform offset rows. The pin height was 0.48 mm, the surface area of each pin was 0.40 $mm^2$, the pin density was 93.5 pins per square centimeter and the total bond or contact area was 37 percent. All of the above pattern rolls had a diameter from raised surface to raised surface of 18.0 centimeters. The anvil roll was constructed from steel, had a smooth surface and a diameter of 18 centimeters. Both of the rolls were heated using an internal hot oil system. The two rolls were adjusted to be in contact with one another and the nip pressure was adjusted as indicated below.

EXAMPLE 1

In this example the pattern roll described above was heated to a temperature of 85 degrees Celsius and the anvil roll was heated to a temperature of 82 degrees Celsius. The nip pressure along the interface between the pattern roll and the anvil roll was 35 psig (4.98 kilograms per lineal millimeter (kg/lmm)). The pattern roll was adjusted to a rotational speed of 6.7 meters per minute and the anvil roll had a rotational speed of 12.2 meters per minute. This resulted in a pattern roll to anvil roll speed ratio of 1.0:1.8. The film unwind had a constant brake tension applied thereto. The inlet speed of the film was 7.3 meters per minute. As a result, the film was being fed into the aperturing assembly while under a slight tension to reduce wrinkling. Once the film exited the aperturing assembly, it was wound up on a winder roll at a rate of 7.9 meters per minute.

Figure 3:
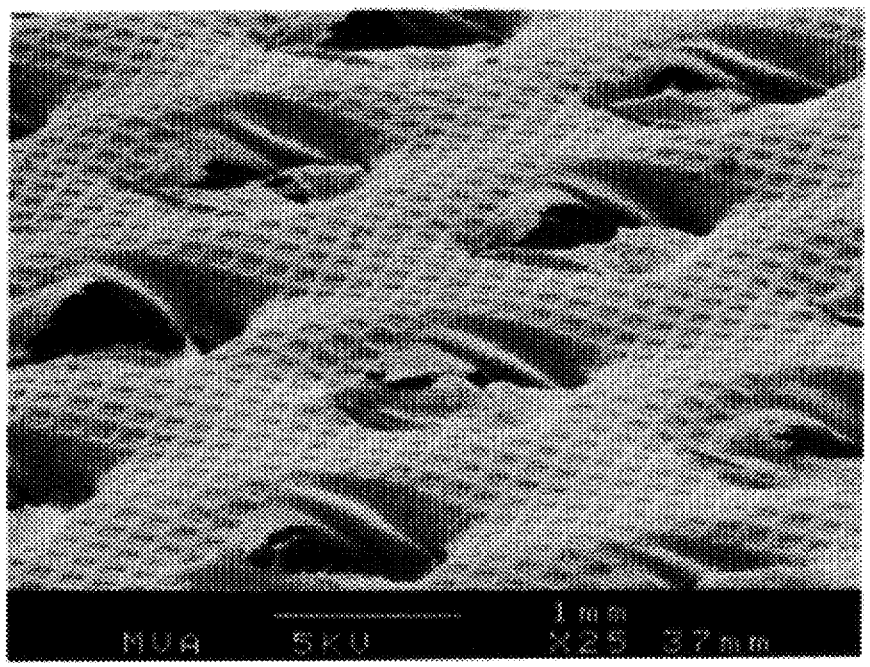
FIG. 3 is a photomicrograph of a film which has been apertured and creped in accordance with the teachings of the present invention. This photomicrograph corresponds to the material described in Example 1.

The resultant film is shown in FIG. 3 of the drawings. As can be seen from the photomicrograph, the film was both apertured and slightly creped. Before processing, the film had a basis weight of 25.4 grams per square meter (gsm) a thickness of 0.025 millimeters and essentially no porosity. After processing, the basis weight increased to 28 grams per square centimeter. Thickness increased to 0.48 millimeters and the porosity was measured to be 6.2 standard cubic meters per minute. The percent open area due to the aperturing was 7 percent which was much less than the 31 percent contact area on the pattern roll thus further demonstrating the creped nature of the resultant web.

The film web of Example 1 was subjected to the profilometry testing outlined above. The average waviness (Wa) of the ten samples was 47.0 microns as measured over a width of approximately 1.25 millimeters and the standard deviation for the ten samples was 17. A plot of the profilometry data is presented in FIG. 8 of the drawings. As can be seen in relation to the other curves, the material of Example 1 (as compared to the below-discussed materials of Examples 2 through 4) was the second smoothest of the materials due to the lower speed differential between the pattern roll and the anvil roll. In addition, the standard deviation was relatively low which indicated that the undulations in the film between the apertures was more uniform than with the other film only materials.

As a point of comparison, two commercially available apertured films were also subjected to the same profilometry testing. The first film was a Driweave body side liner material from an ALWAYS® sanitary napkin manufactured by the Procter and Gamble Company of Cincinnati, Ohio. It had an average surface waviness (Wa) of 53.9 and a standard deviation of 8.9. This material had a higher amplitude but a lower standard deviation thus indicating a more uniform material across the solid film areas between the apertures.

The second material was a vacuum apertured film (Code #2 AIBNN) from the Bi-Plast Company of Pieve Fissiraga (MI), Italy. It had an average surface waviness (Wa) of 27.3 and a standard deviation of 6.7. Here again, this material when compared to the apertured film of Example 1 had a lower standard deviation thus indicating a more uniform film surface between apertures.

EXAMPLE 2

In this example the pattern roll described above was heated to a temperature of 85 degrees Celsius and the anvil roll was heated to a temperature of 82.2 degrees Celsius. The nip pressure along the interface between the pattern roll and the anvil roll was 30 psig (4.23 kg/lmm). The pattern roll was adjusted to a rotational speed of 3.6 meters per minute and the anvil roll had a rotational speed of 12.2 meters per minute. This resulted in a pattern roll/anvil roll speed ratio of 1.0:3.3. The film unwind had a constant brake tension applied thereto. The film inlet speed was 6.1 meters per minute. Once the film exited the aperturing assembly, it was wound up on a winder roll at a rate of 4.3 meters per minute.

Figure 4:
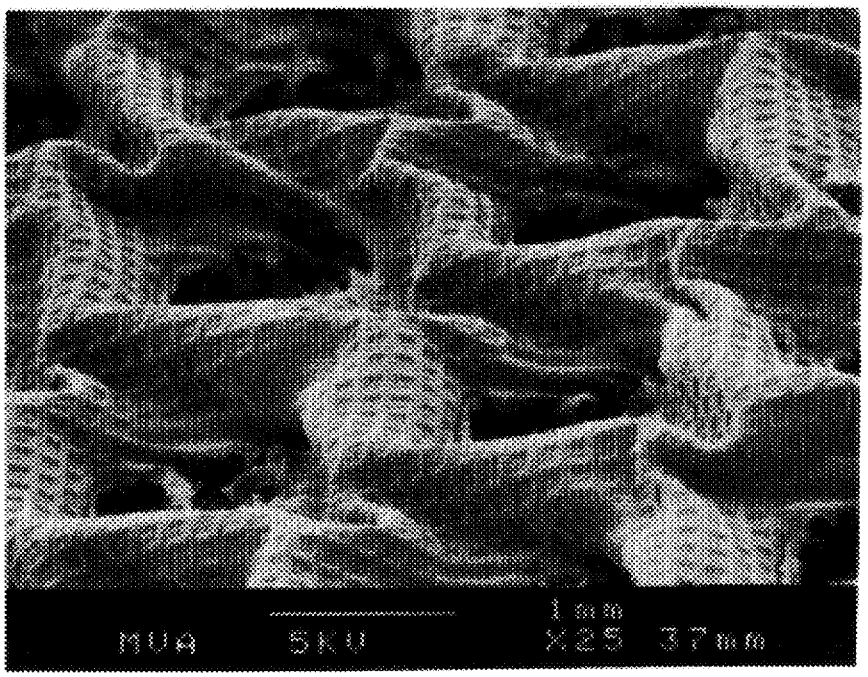
FIG. 4 is a photomicrograph of a film which has been apertured and creped in accordance with the teachings of the present invention. This photomicrograph corresponds to the material described in Example 2.

The resultant film is shown in FIG. 4 of the Drawings. As can be seen from the photomicrograph, the film was both apertured and creped. The creping was much more pronounced than in Example 1 and, as a result of the extra creping, the film exhibited stretch properties in the machine direction. Before processing, the film had a basis weight of 25.4 gsm, a thickness of 0.025 millimeters and essentially no porosity. After processing, the basis weight increased to 41.4 gsm. Thickness increased to 0.84 millimeters and the porosity was measured to be 15.7 standard cubic meters per minute. The percent open area due to the aperturing was 19 percent which once again was less than the contact area (31 percent) of the pattern roll.

The film web of Example 2 was subjected to the profilometry testing outlined above. The average waviness (Wa) of the ten samples was 90.6 microns as measured over a width of approximately 1.25 millimeters and the standard deviation for the ten samples was 42. A plot of the profilometry data is presented in FIG. 8 of the Drawings. As can be seen in relation to the other curves, the material of Example 2 had a higher degree of undulations and a greater average amplitude of the surface waviness (Wa) than the material in Example 1. The standard deviation was also greater thus showing a greater degree of irregularity of the web material between the apertures.

EXAMPLE 3

In this example the pattern roll described above was heated to a temperature of 90.5 degrees Celsius and the anvil roll was heated to a temperature of 76.7 degrees Celsius. The nip pressure along the interface between the pattern roll and the anvil roll was 40 psig (5.74 kg/lmm). The pattern roll was adjusted to a surface rotational speed of 3.0 meters per minute and the anvil roll had a surface rotational speed of 18.3 meters per minute. This resulted in a pattern roll/anvil roll speed ratio of 1.0:6.0. The film unwind had a constant brake tension applied thereto. The film inlet speed was 7.6 meters per minute. Once the film exited the aperturing assembly, it was wound up on a winder roll at a rate of 4.9 meters per minute.

Figure 5:
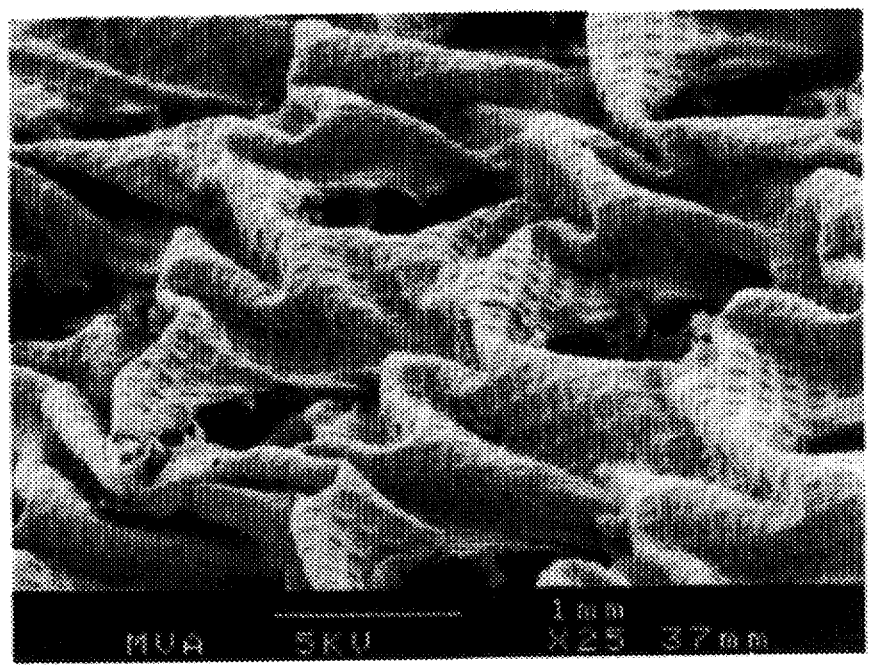
FIG. 5 is a photomicrograph of a film which has been apertured and creped in accordance with the teachings of the present invention. This photomicrograph corresponds to the material described in Example 3.

The resultant film is shown in FIG. 5 of the Drawings. As can be seen from the photomicrograph, the film was both apertured and creped. The creping was more pronounced than in Examples 1 and 2 and as a result of the extra creping, the film exhibited stretch and recovery properties in the machine direction. Before processing, the film had a basis weight of 25.4 gsm, a thickness of 0.025 millimeters and essentially no porosity. After the processing, the basis weight increased to 40.3 gsm. Thickness increased to 0.81 millimeters and the porosity was measured to be 16.9 standard cubic meters per minute. The percent open area due to the aperturing was 20 percent based upon the surface area of the film.

The film web of Example 3 was subjected to the profilometry testing outlined above. The average waviness (Wa) of the ten samples was 106.7 microns as measured over a width of approximately 1.25 millimeters and the standard deviation for the ten samples was 38. A plot of the profilometry data is presented in FIG. 8 of the drawings. As can be seen in relation to the other curves, the material of Example 3 had a higher degree of undulations and a greater average amplitude of the surface waviness (Wa) than the rest of the materials tested. This was due to the much higher speed differential in this example between the pattern roll and the anvil roll. The standard deviation was also high thus showing a greater degree of irregularity of the web material between the apertures as compared to the commercially available materials described above.

EXAMPLE 4

Figure 6:
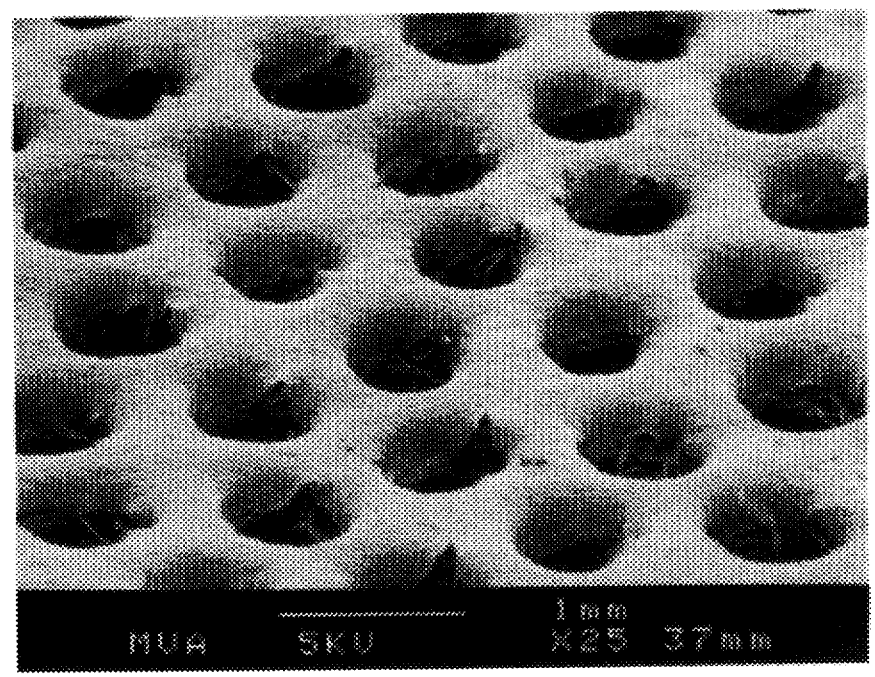
FIG. 6 is a photomicrograph of a film and nonwoven which has been apertured and laminated in accordance with the teachings of the present invention. This photomicrograph corresponds to the material described in Example 4.

In this example the pattern roll described above was heated to a temperature of 85 degrees Celsius and the anvil roll was heated to a temperature of 79.5 degrees Celsius. The nip pressure along the interface between the pattern roll and the anvil roll was 5.03 kg/lmm. The pattern roll was adjusted to a rotational speed of 3.3 meters per minute and the anvil roll had a rotational speed of 18.3 meters per minute. This resulted in a pattern roll/anvil roll speed ratio of 1.0:5.5. The film unwind had a constant brake tension applied thereto. The film had an inlet speed of 3.7 meters per minute. As a result, the film was being fed into the aperturing assembly while under a slight tension to reduce wrinkles. Along with the film, there was also fed into the nip a supply of the above-describe nonwoven from a second unwind at the same speed. The film was positioned adjacent the patterned roll although it should be noted that other aperturing and creping attempts were successful with the film oriented to the anvil roll side of the assembly. The material emerging from the exit side of the nip was a coapertured laminate with the apertures extending through both layers of the laminate. See FIG. 6. Once the film/nonwoven laminate exited the aperturing assembly, it was wound up on a winder roll at a rate of 3.3 meters per minute.

Before the aperturing/bonding process, the film had a basis weight of 18.7 gsm and the nonwoven had a basis weight of 16.6 gsm for a non-bonded combined basis weight of 35.3 gsm. After processing, the basis weight increased to 36.0 gsm. Before processing, the film thickness was 0.019 mm and the nonwoven thickness was 0.43 mm for a combined unbonded thickness of 0.45 mm. After processing, the laminate thickness was 0.33 mm thereby showing a reduction in overall thickness. Porosity went from essentially zero due to the unapertured film to a value of 13.7 standard cubic meters per minute. Open area for the laminate was 16 percent. A notable observation with respect to this example was the lack of residual film around the perimeters of the apertures. On the film only samples (Examples 1 through 3), there was consistently observed the presence of a flap-like member around the perimeter of the apertures. With the coapertured film/nonwoven laminate of Example 4, this flap was not nearly as prevalent. As a result, the material was very soft to the touch with no scratchy surface and this was believed to be attributed to the lack of the residual film flaps. Such a material may be used in a personal care absorbent article such as a sanitary napkin with the film side positioned towards the absorbent core or with the nonwoven positioned towards the absorbent core.

The film and fibrous nonwoven web laminate of Example 4 was subjected to the profilometry testing outlined above. The average waviness (Wa) of the ten samples was 22.0 microns as measured over a width of approximately 1.25 millimeters and the standard deviation for the ten samples was 11. A plot of the profilometry data is presented in FIG. 8 of the drawings. As can be seen in relation to the other curves, the material of Example 4 had a lower degree of undulations and a lower average amplitude of the surface waviness (Wa) than the rest of the materials tested. It is believed that this was due to the cushioning effect the fibrous nonwoven layer had on the film layer even though the speed differential in this example between the pattern roll and the anvil roll was almost as great as that used in Example 3 which did have the greatest average surface waviness. The standard deviation was also low thus showing less irregularity in the surface of the material of the web between the apertures. Here again it is believed that this was due to the cushioning effect of the fibrous nonwoven web layer.

EXAMPLE 5

In this example the pattern roll described above was heated to a temperature of 99 degrees Celsius and the anvil roll was heated to a temperature of 82 degrees Celsius. The nip pressure along the interface between the pattern roll and the anvil roll was 5.74 kg/lmm. The pattern roll was adjusted to a rotational speed of 3.0 meters per minute and the anvil roll had a rotational speed of 18.0 meters per minute. This resulted in a pattern roll to anvil roll speed ratio of 1.0:6.0. The nonwoven unwind had a constant brake tension applied thereto. As a result, the spunbond/meltblown/spunbond (SMS) nonwoven laminate was being fed into the aperturing assembly while under a slight tension and at a speed of 6.1 meters per minute. Once the SMS laminate exited the aperturing assembly, it was wound up on a winder roll at a rate of 3.6 meters per minute.

Figure 7:
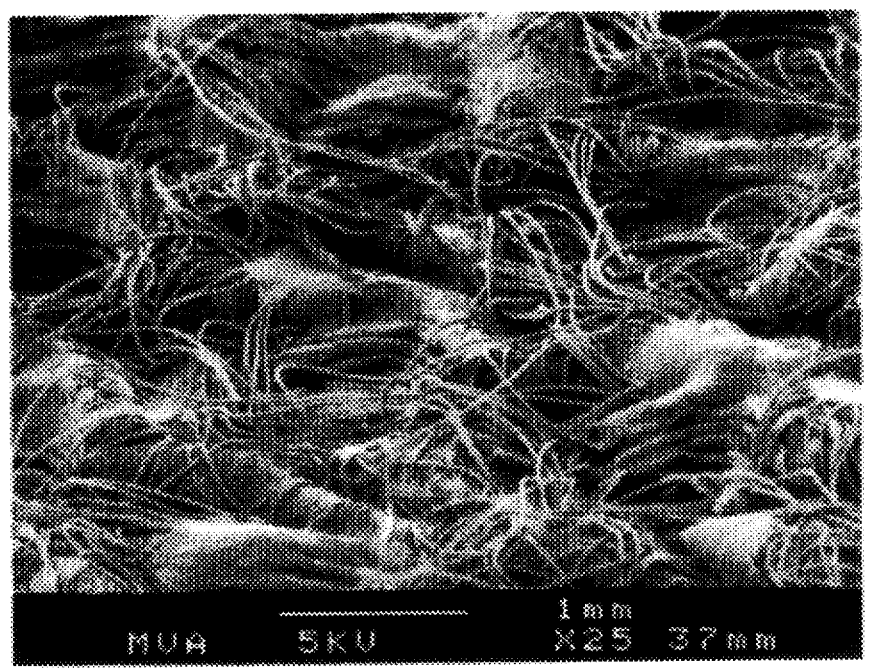
FIG. 7 is a photomicrograph of a nonwoven which has been apertured and creped in accordance with the teachings of the present invention. This photomicrograph corresponds to the material described in Example 5.

The resultant film is shown in FIG. 7 of the drawings. As can be seen from the photomicrograph, the SMS laminate was both apertured and slightly creped with an open area of 12 percent. Before processing, the web had a basis weight of 28.4 gsm, a thickness of 0.228 millimeters and a porosity of 3.8 standard cubic meters per minute. After the processing, the basis weight increased to 36.2 gsm, thickness increased to 0.73 millimeters and the porosity increased to 12.3 standard cubic meters per minute.

As can be seen from the foregoing examples, the process of the present invention is capable of providing a wide variety of materials including single layer materials and laminates which may be creped and/or apertured. These materials can be used in a wide variety of applications, one being as a liner material for a sanitary napkin.

Figure 9:
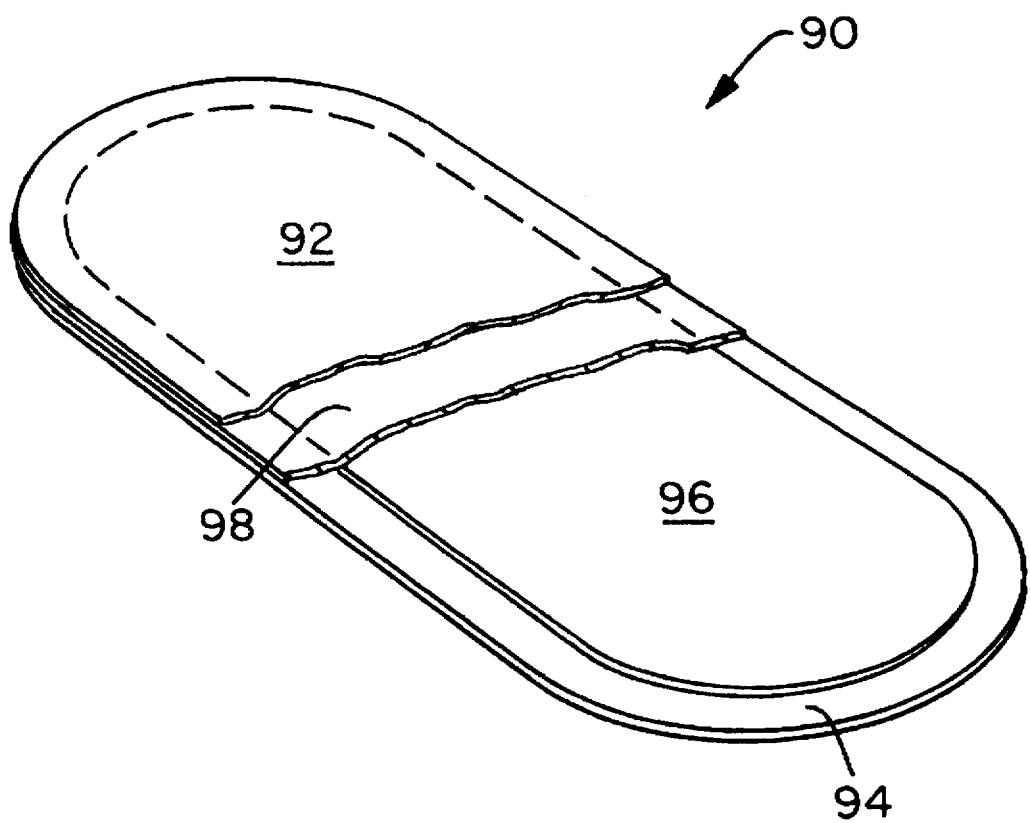
FIG. 9 is a cut-away perspective view of a personal care absorbent article, in this case a sanitary napkin, which utilizes the material of the present invention as the top sheet or body side liner.

A small scale confidential consumer use test was conducted to evaluate one of the materials according to the present invention against a conventional pattern roll faster film cover on a sanitary napkin. Referring to FIG. 9 of the drawings, the personal care absorbent article, which in this case was a sanitary napkin 90, included a liquid pervious top sheet 92 and a bottom sheet 94 with an absorbent core 96 disposed between the top sheet 92 and the bottom sheet 94. The sanitary napkin according to the present invention utilized the apertured and creped film from Example 2 above as the top sheet 92. The second film used for the top sheet 92 was made according to a more conventional process whereby the pattern roll rotates at a faster surface velocity than the anvil roll. Both films were made from the same film composition as was described in Example 2. The preapertured bulk and basis weight for the conventional pattern faster film were 0.0375 millimeters and 37.5 grams per square meter respectively. This film was apertured using the previously described pattern roll with a 31 percent bond area. The pattern roll was rotated approximately two times faster than the anvil roll. The resultant pattern faster film had a final basis weight of 30.5 gsm which was a reduction in basis weight due to the stretching of the film during the aperturing process. The pattern faster film had a bulk of 0.64 millimeters, a 23 percent open area and a porosity of 26.7 cubic meters per minute.

Both sanitary napkins used the same chassis which included an absorbent core 96 made from two layers of wood pulp fluff each weighing 6 grams and with a combine bulk of 9 millimeters. The bottom sheet or baffle 94 was a 0.025 millimeter thick low density polyethylene film. In between the top sheet and the absorbent core there was positioned a 33.2 gsm bicomponent through-air bonded spunbond nonwoven web 98 made from 5 denier polyethylene/polypropylene side-by-side bicomponent fibers which had been treated to render the fibers wettable. The top sheets were placed on top of the spunbond layers and the top sheets and bottom sheets of the sanitary napkins were peripherally sealed to one another.

Twelve napkins of each construction were worn by women with medium to heavy menstrual flows. Each woman wore both constructions for four hours each or until leakage occurred. At the end of each wearing, the women were asked to evaluate each napkin construction for dryness, stain masking, cover cleanliness and absorbency. The sanitary napkin using the top sheet according to the present invention (Example 2) was rated better overall especially in the areas of cover cleanliness and stain masking. The surface of the pattern roll faster top sheet had less three-dimensionality thus resulting in fluid hang-up and a wet surface whereas the material of the present invention did not exhibit these traits. These results were significant considering the fact that the pattern faster film had greater open area and greater porosity. The resilient and irregular surface of the material of the present invention is believed to be especially important in the area of maintaining a clean and dry surface with distancing from the body. Despite the significant land area between the apertures, the highly creped surface topography kept fluid away from the body while transporting the fluid into and through the apertures.

Having thus described the invention in detail, it should be apparent that various modifications and changes can be made in the present invention without departing from the spirit and scope of the following claims.

We claim:

1. A process for forming an apertured web comprising:

a) providing a set of aperturing rolls including a first roll having a patterned surface and a second roll having a flat surface with a nip defined therebetween, b) rotating said first and second roll in opposite directions, said first roll rotating at a first rotational speed and said second roll rotating at a second rotational speed, said second rotational speed being about 1.8 times faster than said first rotational speed, and c) passing a web between said first and second rolls within said nip to form apertures in said web.

2. A process for forming an apertured web comprising:

a) providing a set of aperturing rolls including a first roll having a patterned surface and a second roll having a flat surface with a nip defined therebetween, b) rotating said first and second roll in opposite directions, said first roll rotating at a first rotational speed and said second roll rotating at a second rotational speed, said second rotational speed being about 1.8 to about 6 times faster than said first rotational speed, and c) passing a web between said first and second rolls within said nip to form apertures in said web.

* * * * *

UNITED STATES PATENT AND TRADEMARK OFFICE
CERTIFICATION OF CORRECTION

PATENT NO. : 5,704,101

DATED : January 6, 1998

INVENTOR(S): Majors et al.

It is certified that errors appear in the above-identified patent and that said Letters Patent is hereby corrected as shown below:

Column 4, line 61, "Heating and or cooling" should read --Heating and/or cooling--;
Column 8, line 4, "LLDPE" should read --LDPE--;
Column 11, line 51, "On the film only samples" should read --On the film's only samples--;
Column 12, line 8, "almost a great as" should read --almost as great as--.

Signed and Sealed this

Fourth Day of August, 1998

Attest:

BRUCE LEHMAN

*Attesting Officer*     *Commissioner of Patents and Trademarks*